March 5, 1957 C. M. BERNER Plant Pat. 1,575
AZALEA PLANT
Filed April 25, 1956
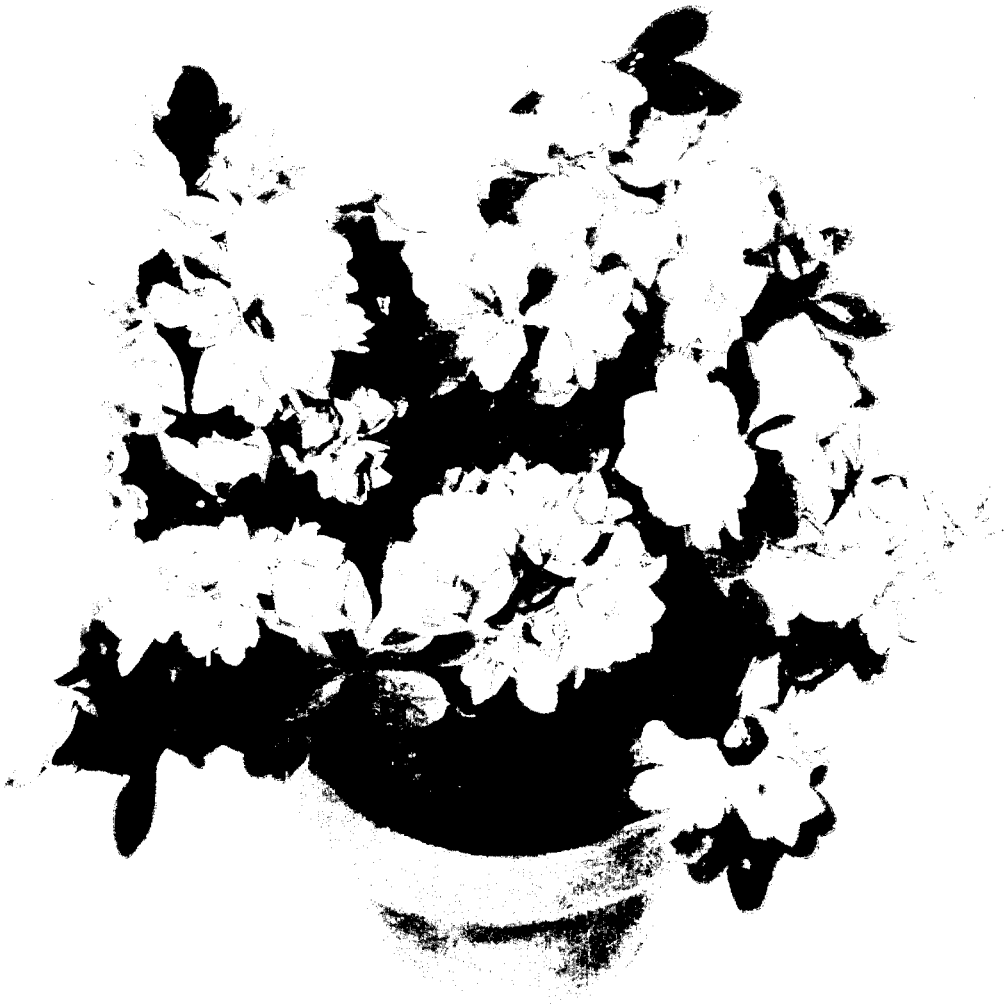
INVENTOR
Charles M. Berner,
BY Raymon E. Rousseau
ATTORNEY.

United States Patent Office

Plant Pat. 1,575
Patented Mar. 5, 1957

1,575

AZALEA PLANT

Charles M. Berner, Cheektowaga, N. Y.

Application April 25, 1956, Serial No. 580,689

1 Claim. (Cl. 47—60)

The present invention relates to a new and distinct variety of Azalea plant of the Kurume type.

This new variety is a sport mutation of an unpatented variety known in the trade as Coral Bells, unpatented.

This new variety was originated and discovered by me in a glass house under by supervision and control at Cheektowaga, Erie County, New York, has been carefully watched, cultivated and nurtured by me, and has been asexually reproduced by me and under my supervision in the above identified glass house by rooting cuttings from the original new plant and by rooting cuttings from each of six successive generations of said plant. Each generation has remained true to its original type and the herein described characteristics through the propagation of two and one-half thousand plants over a period of six years and has shown its qualities and characteristics to be permanently fixed.

In physical structure the main stem or trunk of the plant like its parent, Coral Bells, is strong, rugged and woody, and its many branches grow in irregular directions. However, its branches are much sturdier and stronger than the branches of its parent and its mature, ovate shaped leaves are somewhat darker and heavier than those of its parent. The plant like its parent, is an early to midseason blooming variety which blooms once a year with a profusion of flowers, but whereas the flowers of its parent have two corolla—one telescoped within the other (this type of flower being known as hose in hose), the flowers of my improved plant have three to four larger, deeper colored and shaded corolla or hose telescoped one within the other and appear to be semi-double.

The accompanying drawing illustrates the form and coloring of a typical specimen of my new variety of Azalea plant, the coloring of which is shown as nearly true as is possible in this type of illustration.

The following is a detailed description of my new variety of Azalea plant in which references to the coloring of the plant are based on Ridgway's Color Chart:

*Parentage*

Origin: Sport mutation.
Parent: Azalea plant known as Coral Bells.

*Plant*

Form: Bush—many branches stronger and sturdier than parent; woody stems, Olive Brown (Plate XL); flower stems Courage Green.
Growth habit: Medium; branching; compact.
Rooting: Vigorous; compact.
Blooming habit: Free, resulting in a profusion of blooms.
Blooming season: Early to midseason.
Foliage:
- *Size.*—Medium.
- *Quantity.*—Abundant.
- *Color.*—Young leaves—Deep Turtle Green (Plate XXXII). Mature leaves: top face—Dull Blackish Green (Plate XLI); under face—Deep Dull Yellow Green (Plate XXXII).
- *Shape.*—Ovate.
- *Texture.*—Top face—glossy; under face—rough.
- *Edge.*—Smooth.

*Flowers*

Buds:
- *Size.*—About ¼ inch and gradually growing in length with unfolding of petals.
- *Petals.*—Eosine Pink (Plate I).
- *Set.*—Freely and profusely in first year of growth.

Bloom:
- *Size.*—Large and full, averaging about two inches between opposite tips of petals.
- *Arrangement.*—Three to eight blooms in a cluster on strong medium length stems.
- *Form.*—Three to four corolla to each bloom; semi-double.
- *Color.*—Eosine Pink shaded with Rose Doree (Plate I).
- *Shape.*—Medium depth. Other features of bloom: continuity—once per season; permanence—four to six weeks; non-fading.

Genital organs:
- *Stamens.*—One to two in number; color—Shrimp Pink (Plate I).
- *Stigma.*—Pale Turtle Green (Plate XXXII).
- *Style.*—Hermose Pink (Plate I).
- *Filaments.*—Garnet Brown (Plate I) with white dots.

This plant is a desirable and commercially valuable evergreen Azalea of compact form which has very dark leaves and which is particularly characterized by its production of an abundance of triple and/or quadruple hose in hose pink shaded with rose blooms.

I claim:

A new and distinct variety of Azalea plant substantially as illustrated and described, characterized by its strong and sturdy branches, its very dark green and very heavy leaves, and more particularly by its profusion of large triple and quadruple hose-in-hose pink shaded with rose blooms.

No references cited.